(12) United States Patent
Chen

(10) Patent No.: US 6,656,949 B1
(45) Date of Patent: Dec. 2, 2003

(54) 4-ANILINOFURO [3,2-C] QUINOLINE DERIVATIVES, AND PREPARATION PROCESSES AND USES OF THE SAME

(75) Inventor: Yeh-Long Chen, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 0 days.

(21) Appl. No.: 10/241,739

(22) Filed: Sep. 12, 2002

(65) Prior Publication Data (65)

(51) Int. Cl.$^7$ ............... A61K 31/4741; C07D 491/048; A61P 35/00
(52) U.S. Cl. ......................... 514/291; 546/89
(58) Field of Search ............... 546/89; 514/291

(56) References Cited

U.S. PATENT DOCUMENTS 2,650,229 A * 8/1953 Timmler ............ 546/64
3,631,050 A * 12/1971 Elslager ............ 546/89

* cited by examiner

*Primary Examiner*—Evelyn Mei Huang
(74) *Attorney, Agent, or Firm*—Baker Botts L.L.P.

(57) ABSTRACT

Disclosed herein are novel 4-anilinofuro[3,2-c]quinoline derivatives of formula (I):

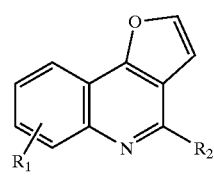

(I)

wherein each of the substituents is given the definition as set forth in the Specification and Claims.

Also disclosed are the preparation process of these derivatives, and their uses in the manufacture of pharmaceutical compositions.

27 Claims, No Drawings

4-ANILINOFURO [3,2-C] QUINOLINE DERIVATIVES, AND PREPARATION PROCESSES AND USES OF THE SAME

BACKGROUND OF THE INVENTION

1) Field of the Invention

The present invention relates to novel 4-anilino[3,2-c] quinoline derivatives, which are found to have the ability to inhibit the growth of a variety of tumor/cancer cells (particularly melanoma cell lines UACC-62 and UACC-257, and one of the renal cancer cell lines, i.e. UO-31), the preparation processes of these derivatives, and their uses in the manufacture of pharmaceutical compositions.

2) Description of the Related Art

Acridine derivatives, especially 9-anilinoacridines, have been extensively studied as potential chemotherapeutic agents due to their capability of intercalating DNA leading to the inhibition of mammalian topoisomerase II (Atwell, G. J. et. al., *J. Med. Chem.* 1972, 15, 611–615; Denny, W. A. et. al., *J. Med. Chem.* 1978, 21, 5–10; Denny, W. A. et. al., *J. Med. Chem.* 1982, 25, 276–315; Gamage, S. A. et. al., *J. Med. Chem.* 1994, 37, 1486–1494; Gamage, S. A. et. al., *J. Med. Chem.* 1997, 40, 2634–2642). In these published articles, 4'-(9-acridinylamino) methanesulfonyl-m-anisidine (amsacrine, m-AMSA) is reported to be specifically relevant and has become a useful clinical drug for the treatment of leukemia and lymphoma (Atwell, G. J. et. al., *J. Med. Chem.* 1972, 15, 611–615).

A tremendous amount of effort has been directed toward the design and preparation of new amsacrine analogues with the aim of developing new drug candidates with an improved broad spectrum of antitumor activity (Baguley, B. C. et. al., *J. Med. Chem.* 1981, 24, 520–525; Rewcastle, G. W. et. al., *J. Med. Chem.* 1986, 29, 472–477; Denny, W. A. et. al., *J Med. Chem.* 1987, 30, 658–663; Su, T. L. et. al., *J. Med. Chem.* 1995, 38, 3226; Stanslas, J. et. al., *J. Med. Chem.* 2000, 43, 1563–1572).

However, the above-mentioned studies focused only on the 9-anilinoacridine skeleton, with a wide variety of substituents on anilino- and/or acridine chromophore. No attempt has been carried out concerning the replacement of acridine with its isosteric 4-anilinofuro[3,2-c]quinoline ring which constitutes an important group of natural products (Moulis, C. et. al., *Phytochemistry* 1983, 22, 2095 Reisch, J. and Iding, M., *Montash. Chem.* 1989, 120, 363).

SUMMARY OF THE INVENTION

Therefore, in the first aspect of this invention, the present invention provides novel 4-anilino[3,2-c]quinoline derivatives of formula (I):

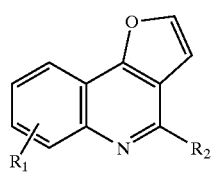

(I)

wherein
$R_1$ represents: H, halogen, OH, $NO_2$, $NH_2$, a $C_1$–$C_4$ alkyl group, or a $C_1$–$C_4$ alkoxy group;

$R_2$ represents a group of the following formula:

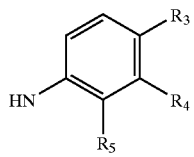

wherein
two of $R_3$, $R_4$, and $R_5$ are H, and the other is

wherein
X represents O, S, NH, or NOR, R in NOR being H or a $C_1$–$C_4$ alkyl group; and
$R_6$ represents H or a $C_1$–$C_4$ alkyl group.

In the second aspect, the present invention provides a pharmaceutical composition which comprises the above-described derivative, in its free type or a pharmaceutically acceptable salt thereof, as an active ingredient in inhibiting the growth of tumor/cancer cells, especially melanoma and renal cancer cells.

In the third aspect, the present invention provides processes for preparing the above-described derivatives of formula (I), as well as their intermediate compounds.

In particular, the present invention provides processes for preparing a compound of formula (I'):

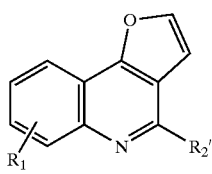

(I')

wherein
$R_1$ represents: H, halogen, OH, $NO_2$, $NH_2$, a $C_1$–$C_4$ alkyl group, or a $C_1$–$C_4$ alkoxy group;
$R_2'$ represents a group of the following formula:

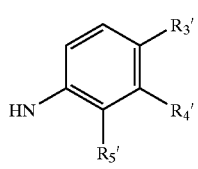

wherein
two of $R_3'$, $R_4'$ and $R_5'$ are H, and the other is

wherein $R_6$ represents H or a $C_1$–$C_4$ alkyl group;
the process comprising the step of reacting a compound of formula (A):

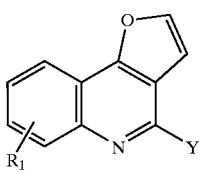

(A)

wherein
$R_1$ is the same as that defined for formula (I'); and
Y represents: Cl, Br, or I;
with a compound of formula (B):

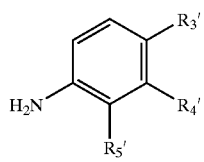

(B)

wherein
$R_3'$, $R_4'$ and $R_5'$ are the same as those defined for formula (I').

The above and other objects, features and advantages of the present invention will become apparent with reference to the following detailed description of the preferred examples.

DETAILED DESCRIPTION OF THE INVENTION

After a variety of studies, the Applicant discovered a novel 4-anilino [3,2-c]quinoline derivative:

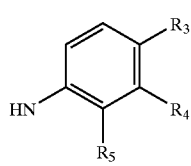

(I)

wherein
$R_1$ represents: H, halogen, OH, $NO_2$, $NH_2$, a $C_1$–$C_4$ alkyl group, or a $C_1$–$C_4$ alkoxy group;
$R_2$ represents a group of formula:

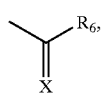

wherein
two of $R_3$, $R_4$, and $R_5$ are H, and the other is

wherein
X represents O, S, NH, or NOR, R in NOR being H or a $C_1$–$C_4$ alkyl group; and
$R_6$ represents H or a $C_1$–$C_4$ alkyl group.

Preferably, $R_1$ is H.
Preferably, $R_6$ is $CH_3$.
In a preferred embodiment, $R_3$ and $R_5$ are H, and $R_4$ is

In a more preferred embodiment, $R_3$ and $R_5$ are H, and $R_4$ is

In still another preferred embodiment, $R_3$ and $R_5$ are H, and $R_4$ is

In yet another preferred embodiment, $R_3$ and $R_5$ are H, and $R_4$ is

In a further preferred embodiment, $R_3$ and $R_5$ are H, and $R_4$ is

wherein R is H or a $C_1$–$C_4$ alkyl group, and, more preferably, R is $CH_3$.

In a preferred embodiment, $R_4$ and $R_5$ are H, and $R_3$ is

In a more preferred embodiment, $R_4$ and $R_5$ are H, and $R_3$ is

In still another preferred embodiment, $R_4$ and $R_5$ are H, and $R_3$ is

In yet another preferred embodiment, $R_4$ and $R_5$ are H, and $R_3$ is

In a further preferred embodiment, $R_4$ and $R_5$ are H, and $R_3$ is

wherein R is H or a $C_1$–$C_4$ alkyl group, and, more preferably, R is $CH_3$.

In a preferred embodiment, $R_1$, $R_2$ and $R_3$ are all H, and $R_4$ is selected from the group consisting of:

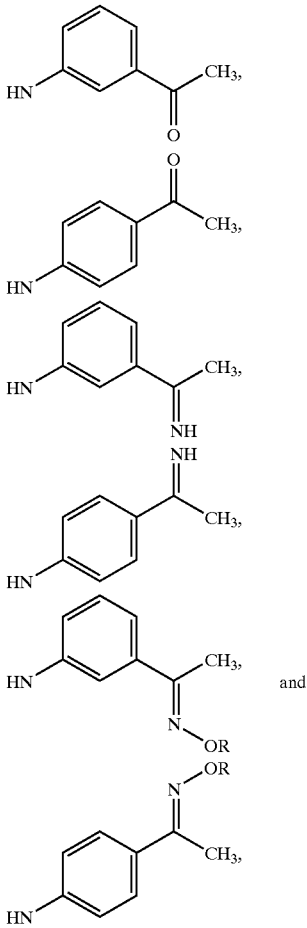

wherein R is H or a $C_1$–$C_4$ alkyl group.

Through in vitro antitumor activity assay, the compound of formula (I) according to the present invention has been found to exhibit inhibitory activities against the growth of a variety of tumor/cancer cells, especially melanoma and renal cancer cells. Therefore, the present invention also envisions the application of the compounds of formula (I) of this invention or the pharmaceutically acceptable salts thereof in the manufacture of antitumor or anticancer compositions.

Therefore, a pharmaceutical composition according to the present invention comprises a compound of formula (I) as described above or the pharmaceutically acceptable salts thereof, and optionally, a pharmaceutically acceptable carrier.

As used herein, the pharmaceutically acceptable salts include salts with inorganic acids, such as hydrochloride, hydrobromide, sulfate, and phosphate; those with organic acids, such as acetate, maleate, tartrate, methanesulfonate; and those with amino acids, such as arginine, aspartic acid and glutamic acid.

The compounds of the present invention may also be present as a hydrate or as a stereoisomer. Therefore, it is contemplated that these hydrates and stereoisomers fall within the technical concept of the present invention.

As stated above, the pharmaceutical composition according to this invention may additionally comprise a pharmaceutically acceptable carrier widely employed in the art for the manufacture of medicaments. For example, the pharmaceutically acceptable carrier can include one or more of the following reagents: solvents, disintegrating agents, binders, excipients, lubricants, absorption delaying agents and the like.

The pharmaceutical composition according to this invention may be administered parenterally or orally in a suitable pharmaceutical form. Suitable pharmaceutical forms include sterile aqueous solutions or dispersions, sterile powders, tablets, troches, pills, capsules, and the like. In addition, the active compounds of the present invention may be incorporated into sustained-release preparations and formulations. Optionally, the pharmaceutical composition according to this invention may be administered alone or in conjunction with an additional anticancer agent, such as Mitomycin, Adriamycin, Actinomycin, cis-platin and the like.

The novel compound of the present invention may be prepared according to the following reaction schemes and protocols.

According to this invention, there is provided a process for producing a compound of formula (I'):

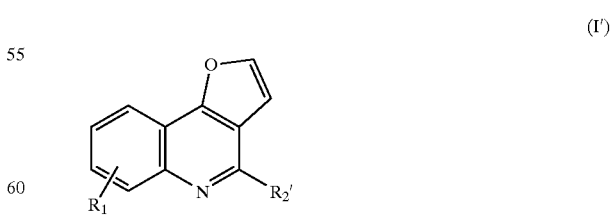

(I')

wherein $R_1$ represents: H, halogen, OH, $NO_2$, $NH_2$, a $C_1$–$C_4$ alkyl group, or a $C_1$–$C_4$ alkoxy group;

R$_2$' represents a group of the following formula:

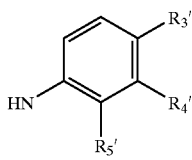

wherein
two of R$_3$', R$_4$' and R$_5$' are H, and the other is

wherein R$_6$ represents H or a C$_1$–C$_4$ alkyl group;
the process comprising the step of: reacting a compound of formula (A):

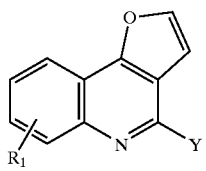

(A)

wherein
R$_1$ is the same as that defined for formula (I'); and
Y represents: Cl, Br, or I;
with a compound of formula (B):

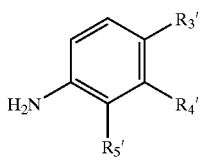

(B)

wherein
R$_3$', R$_4$' and R$_5$' are the same as those defined for formula (I').
Preferably, the compound of formula (A) is

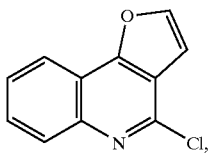

and this compound is formed from the reaction of

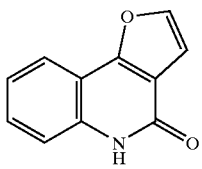

and POCl$_3$.

Optionally,

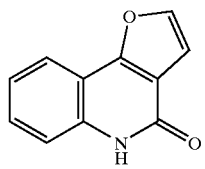

may be reacted with POCl$_3$ and PCL$_5$, or with SOCl$_2$ in the presence of DMF, to thereby produce

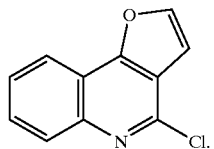

Concerning the preparation of

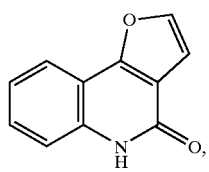

reference is made to, for example, the following prior methods:

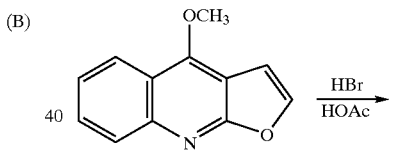

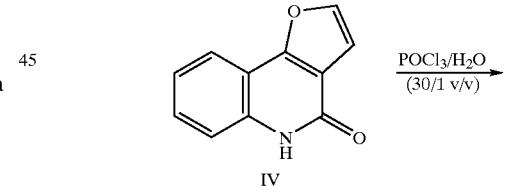

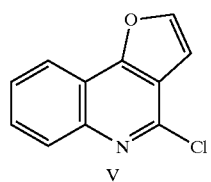

(see Tuppy, H. and Bohm, F., *Monatsh.* 1956, 87, 735–740)

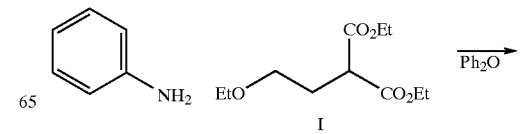

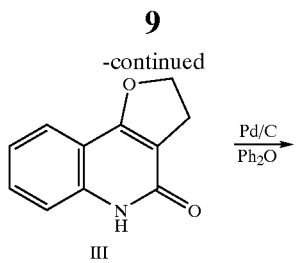

III

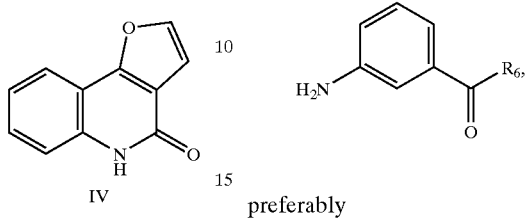

IV (see Grundon, M. F. et al. *J. Chem. Soc.* 1955, 4284–4290)

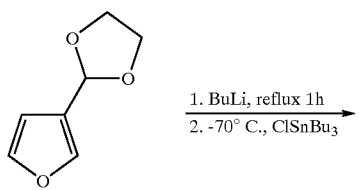

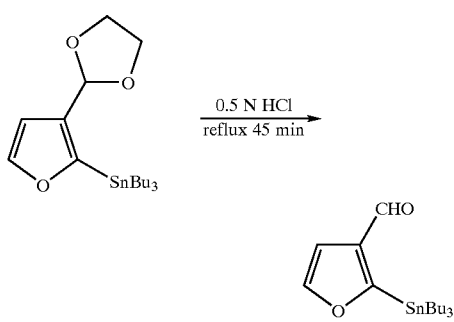

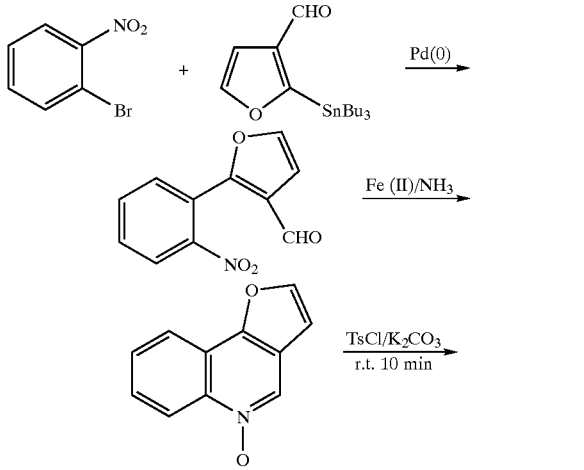

(see Gronowits, S. et al. *J. Hterocyclic Chem.*, 1990, 27, 1159–1160)

Preferably, the compound of formula (B) is o-, m-, or p-aminoacetophenone. The aminoacetophenone compound may be chemically modified according to the prior methods, so that the methyl group present thereon is extended to a larger alkyl group (Doud, et al. *J. Am. Chem. Soc.* 1958, 80, 2205–2210).

In a preferred embodiment, the compound of formula (B) is

preferably

In another preferred embodiment, the compound of formula (B) is

preferably

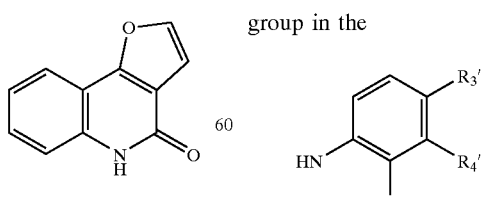

In a preferred embodiment, the resultant compound of formula (I') according to the present process is further treated with a compound of formula $NH_2OR$, in which R is H or a $C_1$–$C_4$ alkyl group, such that the group in the group of the compound of formula (I') is chemically modified to a

group, wherein R is H or a $C_1$-$C_4$ alkyl group.

The compound of formula $NH_2OR$ may be prepared, e.g. according to the following prior method:

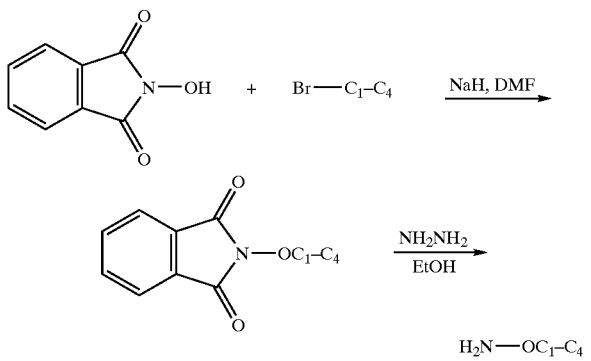

(see Kim, J. N. et al., *Synth. Commun.*, 1992, 22, 1427–1432).

In another preferred embodiment, the resultant compound of formula (I') according to the present process is further treated with a Lawesson's reagent or $P_2S_5$, such that the

group in the

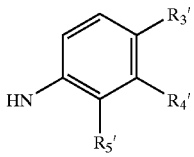

group of the compound of formula (I') is chemically modified to a

group.

The chemical name of the Lawesson's reagent is 4-methoxyphenylthiophosphine, which has the following structural formula:

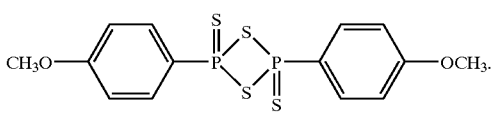

The Lawesson's reagent is a commercial product available from Robinson Brothers Limited and may be used according to the manufacturer's recommendations as posted on the internet website.

In another preferred embodiment, the resultant compound of formula (I') according to the present process is further treated with benzyldimethylphosphinimide, such that the

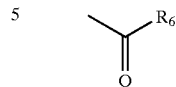

group in the

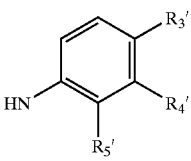

group of the compound of formula (I') is chemically modified to a

group.

Concerning the use of benzyldimethylphosphinimide in the above chemical modification, reference is made to Wannagat, U.; Muenstedt, R. *Phosphorus Sulfur*, 1987, 29, 233–238.

In another preferred embodiment, the resultant compound of formula (I') according to the present process is further treated with $NH_2OH$ to chemically modify the

group in the

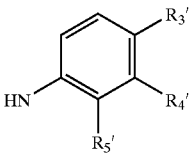

group of the compound of formula (I') to a

group, followed by a treatment with a $C_1$-$C_4$ alkyl halide, to thereby modify the

group to a

group, wherein R is a $C_1$–$C_4$ alkyl group.

In order to more clearly describe the present invention, the following demonstration uses

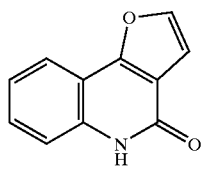

as the starting material, and the novel 4-anilino[3,2-c]quinoline derivatives of the present invention may be produced according to the following synthesis scheme:

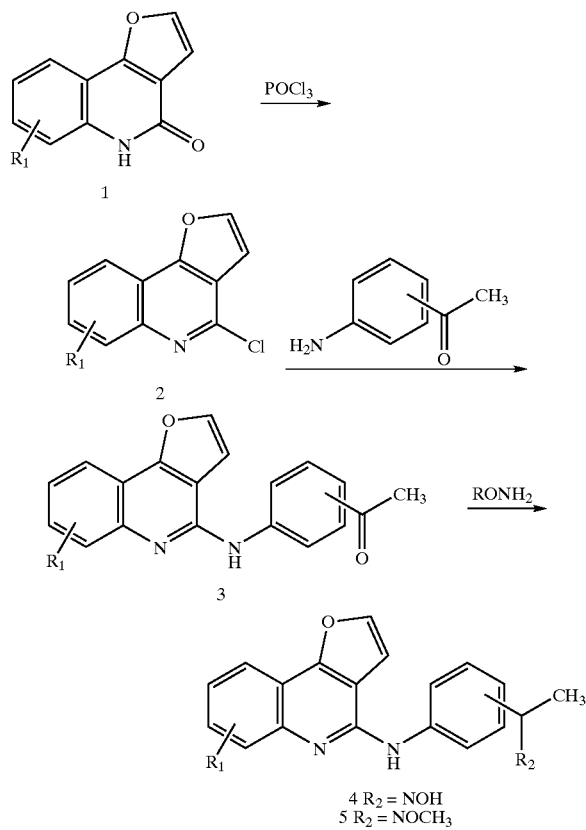

First, the known compound 5H-furo[3,2-c]quinolin-4-one (compound 1) is reacted with $POCl_3$ to produce 4-chlorofuro[3,2-c]quinoline (compound 2). Compound 2 is further reacted with 3-aminoacetophenone in a solution of EtOH-$H_2$ (2:1) to yield 1-[3-chlorofuro[3,2-c]quinolin-4-ylamino] phenyl)ethanone (compound 3).

The resultant Compound 3 may be further reacted with hydroxylamine or O-methylhydroxylamine to yield 1-[3-(furo[3,2-c]quinolin-4-ylamino) phenyl]ethanone oxime (compound 4) or 1-[3-(furo[3,2-c]quinolin-4-ylamino) phenyl]ethanone O-methyloxime (compound 5), respectively.

The 3-aminoacetophenone suitable for use in the synthesis of the above compound 3 is commercially available from Japan TCI Tokyo Kasei Kogyo Co., Ltd. In addition to 3-aminoacetophenone, the p- and m-stereoisomers thereof may be used in the synthesis scheme described above.

The hydroxylamine hydrochloride suitable for use in the synthesis of the above compound 4 is a commercial product available from, e.g. England Lancater Synthesis Ltd.

The invention will now be described in more detail with reference to the following examples. However, it should be understood that these examples are given solely for the purpose of illustration and are not intended to limit the scope of the present invention.

EXAMPLES

Each of the melting points shown in the following examples was detected by an uncorrected Electrothermal IA9100 digital melting-point apparatus. The column chromatography was performed using silica gel 60 (sieve mesh 230–400 mm, manufactured by E. Merck Company) as the solid phase in combination with a suitable eluent for separation and purification. $^1$H-NMR spectra were detected using a Varian Unity-400 (400 $MH_z$) or Varian Gemini-200 (200 $MH_z$) nuclear magnetic resonance spectrometer, with chemical shifts being represented by δ in ppm using TMS (0 ppm) as an internal standard, and coupling constants being represented by J in Hz. Elemental analyses were carried out on a Heraeus CHN-O-Rapid elemental analyzer, and results were within ±0.4% of calc. values.

Example 1

4-Chlorofuro[3,2-c]quinoline (Compound 2)

A mixture of 5H-furo[3,2-c]quinolin-4-one (compound 1 prepared according to the aforesaid prior method, 0.22 g, 1.19 mmol), 4 ml of $POCl_3$, and 1 ml of $Et_3N$ was refluxed for 8 hours. 20 ml of ice/water was added into the cold reaction mixture, followed by neutralizing the same with 10N NaOH solution. A brown precipitate was collected by filtration, washed with cold water, and purified by column chromatography (using $CH_2Cl_2$ as an eluent) to obtain 4-chlorofuro[3,2-c]quinoline (Compound 2, 0.21 g, 86% yield).

Detected Properties of the Title Compound:

Mp: 120–122° C. $^1$H NMR (200 MHz, $CDCl_3$) δ 7.03 (d, 1H, J=2.2 Hz), 7.64 (m, 1H), 7.73 (m, 1H), 7.82 (d, 1H, J=2.2 Hz), 8.14 (dd, 1H, J=8.0, 2.0 Hz), 8.25 (dd, 1H, J=7.4, 2.0 Hz). $^{13}$C NMR (50 MHz, $CDCl_3$): δ 106.33, 116.65, 119.80, 120.11, 127.19, 128.81, 129.21, 144.29, 145.03, 145.22, 156.38.

Example 2

1-[3-Chlorofuro[3,2-c]quinolin-4-ylamino]phenyl) ethanone (Compound 3)

Concentrated HCl was added to a solution of 4-chlorofuro [3,2-c]quinoline (Compound 2, 408 mg, 2 mmol) and 3-aminoacetophenone (406 mg, 3 mmol) until a pH of 6 is reached. The mixture was refluxed for 40 minutes, and the solvent was then evaporated in vacuo to result in a residual solid, which was suspended in 40 ml of ice-water and neutralized with 2N NaOH solution. The resultant precipitate was collected by filtration and purified by flash column chromatography (silica gel, n-hexane/ethyl acetate (2:1) as an eluent) to obtain 1-[3-chlorofuro[3,2-c]quinolin-4-ylamino]phenyl)ethanone (602 mg, 99% yield).

Detected Properties of the Title Compound:

Mp: 233–234° C.; $^1$H NMR (200 MHz, DMSO-d$_6$) δ 2.65 (s, 3H), 7.66 (m, 3H), 7.78 (d, 1H, J=2.0 Hz), 8.00 (m, 3H), 8.19 (dd, 1H, J=8.0, 1.2 Hz), 8.36 (m, 2H), 11.60 (br s, 1H); $^{13}$C NMR (50 MHz, DMSO-d$_6$) δ 26.87, 107.23, 110.97, 113.15, 120.19, 121.11, 123.35, 125.34, 125.78, 128.19, 130.06, 130.45, 137.29, 137.70, 138.05, 146.71, 148.61, 156.09, 197.52. Anal. Calcd for C$_{19}$H$_{14}$N$_2$O$_2$.HCl: C, 67.36; H, 4.46; N, 8.27. Found: C, 67.02; H, 4.49; N, 8.19.

Example 3

1-[3-(Furo[3,2-c]quinolin-4-ylamino)phenyl]ethanone (Compound 4)

70 mg of hydroxylamine hydrochloride was added into a suspension of 1-[3-furo[3,2-c]quinolin-4-ylamino]phenyl]ethanone (Compound 3, 151 mg, 0.50 mmol) in EtOH (5 ml). The reaction mixture was refluxed for 30 minutes, and the solvent was then removed in vacuo to result in a residual solid, which was subsequently suspended in water (20 ml). The resultant precipitate was collected by filtration and crystallized from MeOH to obtain 1-[3-(furo[3,2-c]quinolin-4-ylamino)phenyl]ethanone (compound 4).

Detected Properties of the Title Compound:

Mp: 164° C. dec.; $^1$H NMR (200 MHz, DMSO-d$_6$) δ 2.21 (s, 3H), 7.50 (m, 3H), 7.64 (d, 1H, J=2.0 Hz), 7.70 (m, 1H), 7.91 (m, 2H), 8.12 (m, 2H), 8.28 (d, 1H, J=2.0 Hz), 10.65 (br s, 1H), 11.29 (br s, 1H); $^{13}$C NMR (50 MHz, DMSO-d$_6$) δ 11.58, 106.61, 110.99, 113.48, 119.88, 121.97, 122.38, 122.59, 124.57, 129.27, 129.78, 138.00, 146.10, 148.72, 152.64, 155.76. Anal. Calcd for C$_{19}$H$_{15}$N$_3$O$_2$.0.7HCl: C, 66.56; H, 4.62; N, 12.25. Found: C, 66.28; H, 4.85; N, 12.00.

Example 4

1-[4-(Furo[3,2-c]quinolin-4-ylamino)phenyl]ethanone O-methyloxime (Compound 5)

Compound 5 was prepared according to the procedures set forth in the above Example 3, except that 40% O-methylhydroxylamine hydrochloride was used in place of hydroxylamine hydrochloride, resulting in a yield of 87%.

Detected Properties of the Title Compound:

Mp: 222–223° C. (MeOH); $^1$H NMR (400 MHz, DMSO-d$_6$) δ 2.23 (s, 3H), 3.94 (s, 3H), 7.56 (m, 2H), 7.63 (m, 1H), 7.72 (m, 2H), 7.84 (m, 1H), 7.97 (d, 1H, J=8.4 Hz), 8.06 (m, 1H), 8.16 (d, 1H, J=8.0 Hz), 8.32 (d, 1H, J=1.2 Hz), 11.38 (br s, 1H); $^{13}$C NMR (100 MHz, DMSO-d$_6$) δ 12.34, 61.68, 107.12, 110.90, 113.15, 120.13, 120.93, 123.42, 124.19, 125.15, 129.70, 130.34, 137.21, 146.57, 148.67, 153.66, 155.99. Anal. Calcd for C$_{20}$H$_{17}$N$_3$O$_2$.HCl: C, 65.31; H, 4.93; N, 11.42. Found: C, 64.99; H, 5.02; N, 11.21.

In order to determine the biological activities of the 4-anilino[3,2-c]quinoline derivative of formula (I) according to the present invention, the following pharmaceutical activity assay was performed.

In Vitro Anticancer Assay

The compounds prepared from the aforesaid Examples 2, 3, and 4 were subjected to in vitro assay to determine whether or not they exhibit the activity of inhibiting the growth of any of the 60 human tumor cell lines derived from 9 cancer cell types.

The tumor cell lines are as follows: (1) CCRF-CEM, HL-60 (TB), K-562, MOLT-4, RPMI-8226, and SR of leukemia, (2) A549/ATCC, EKVX, HOP-62, HOP-92, NCI-H226, NCI-H23, NCI-H322M, and NCI-H522 of non-small cell lung cancer, (3) COLO 205, HCC-2998, HCT-116, HCT-15, HT29, KM12, and SW-620 of colon cancer, (4) SF-268, SF-295, SF-539, SNB-19, SNB-75, and U251 of CNS cancer, (5) LOX IMVI, MALME-3M, M14, SK-MEL-2, SK-MEL-28, SK-MEL-5, UACC-62, and UACC-257 of melanoma, (6) IGROV1, OVCAR-3, OVCAR-4, OVCAR-5, OVCAR-8, and SK-OV-3 of ovarian cancer, (7) 786-0, A498, ACHN, CAKI-1, RXF 393, SN12C, TK-10, and UO-31 of renal cancer, (8) PC-3 and DU-145 of prostate cancer, and (9) MCF7, MCF7/ADR-RES, MDA-MB-231/ATCC, HS 578T, MDA-MB-435, MDA-N, and T-47D of breast cancer.

For each compound, dose-response curves for each cell line were measured with five different drug concentrations, and the concentration causing 50% cell growth inhibition (GI$_{50}$) compared with the control was calculated.

Table 1 summarizes the respective GI$_{50}$ values and the mean GI$_{50}$ values of the compounds of Examples 2, 3, and 4 in relation to all the 60 tumor cell lines.

TABLE 1[a]

| Tumor/cancer | Compound 3 | Compound 4 | Compound 5 |
|---|---|---|---|
| Leukemia | 91.2 | 9.26 | 15.4 |
| Lung Cancer | 15.49 | 8.98 | 10.8 |
| Colon Cancer | 42.8 | 10.3 | 10.3 |
| CNS Cancer | 19.1 | 14.8 | 14.8 |
| Melanoma | 40.2 | 9.82[b] | 11.0[d] |
| Ovarian Cancer | 28.4 | 14.5 | 15.2 |
| Renal Cancer | 16.1 | 10.3[c] | 10.1[e] |
| Prostate Cancer | 32.5 | 12.7 | 15.2 |
| Breast Cancer | 34.0 | 12.0 | 13.1 |
| Mean[f] | 22.5 | 7.80 | 8.78 |

[a]Data obtained from NCI's in vitro disease-oriented tumor cells screen. GI$_{50}$Drug molar concentration causing 50% cell growth inhibition.
[b]Selective cytotoxicity was observed, especially potent against UACC-257 (GI$_{50}$ < 0.01) and UACC-62 (GI$_{50}$ < 0.01).
[c]Selective cytotoxicity was observed, especially potent against UO-31 (GI$_{50}$ = 0.030).
[d]Selective cytotoxicity was observed, especially potent against UACC-257 (GI$_{50}$ = 0.042) and UACC-62 (GI$_{50}$ < 0.01).
[e]Selective cytotoxicity was observed, especially potent against UO-31 (GI$_{50}$ < 0.01).
[f]Mean values over 60 cell lines tested.

All patents and references cited in the present specification are hereby incorporated by reference in their entirety. In case of conflict, the present description, including definitions, will prevail.

While the invention has been described with reference to the above specific embodiments, it is apparent that numerous modifications and variations can be made without departing from the scope and spirit of this invention. It is therefore intended that this invention be limited only as indicated by the appended claims.

I claim:

1. A compound of formula (I) or a pharmaceutically acceptable salt thereof:

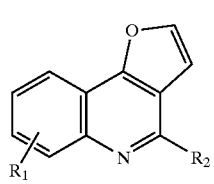

(I)

wherein

R$_1$ represents: H, halogen, OH, NO$_2$, NH$_2$, a C$_1$–C$_4$ alkyl group, or a C$_1$–C$_4$ alkoxy group;

$R_2$ represents a group of the following formula:

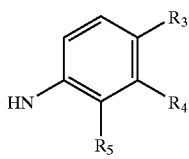

wherein two of $R_3$, $R_4$ and $R_5$ are H, and the other is

wherein

X represents O, S, NH, or NOR, R in NOR being H or a $C_1$–$C_4$ alkyl group; and $R_6$ represents H or a $C_1$–$C_4$ alkyl group.

2. The compound as claimed in claim 1, wherein $R_1$ is H.

3. The compound as claimed in claim 1, wherein $R_6$ is $CH_3$.

4. The compound as claimed in claim 1, wherein $R_3$ and $R_5$ are H, and $R_4$ is

5. The compound as claimed in claim 4, wherein X is O.

6. The compound as claimed in claim 4, wherein X is S.

7. The compound as claimed in claim 4, wherein X is NH.

8. The compound as claimed in claim 4, wherein X is NOR, R in NOR being H or a $C_1$–$C_4$ alkyl group.

9. The compound as claimed in claim 8, wherein X is $NOCH_3$.

10. The compound as claimed in claim 1, wherein $R_4$ and $R_5$ are H, and $R_3$ is

11. The compound as claimed in claim 10, wherein X is O.

12. The compound as claimed in claim 10, wherein X is S.

13. The compound as claimed in claim 10, wherein X is NH.

14. The compound as claimed in claim 10, wherein X is NOR, R in NOR being H or a $C_1$–$C_4$ alkyl group.

15. The compound as claimed in claim 14, wherein X is $NOCH_3$.

16. The compound as claimed in claim 1, wherein $R_1$, $R_2$, and $R_3$ are H, and $R_4$ is selected from the group consisting of:

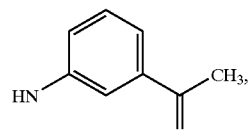

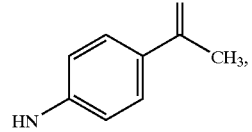

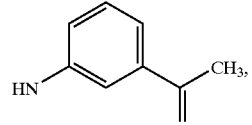

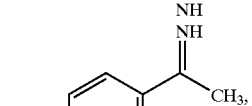

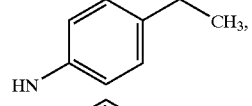

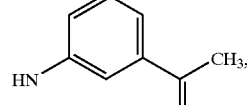

and

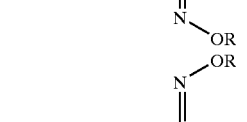

wherein R is H or a $C_1$–$C_4$ alkyl group.

17. A pharmaceutical composition comprising a compound of formula (I) as claimed in claim 1 or a pharmaceutically acceptable salt thereof, and, optionally a pharmaceutically acceptable carrier.

18. A pharmaceutical composition of claim 17 for use in inhibiting the growth of tumor/cancer cells.

19. A process for producing a compound of formula (I'),

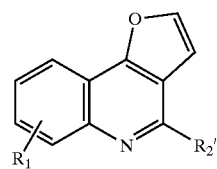

(I')

wherein $R_1$ represents: H, halogen, OH, $NO_2$, $NH_2$, a $C_1$–$C_4$ alkyl group, or a $C_1$–$C_4$ alkoxy group;

$R_2'$ represents a group of the following formula:

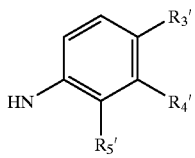

wherein two of $R_3'$, $R_4'$ and $R_5'$ are H, and the other is

wherein $R_6$ represents H or a $C_1$–$C_4$ alkyl group;

said process comprising the step of: reacting a compound of formula (A):

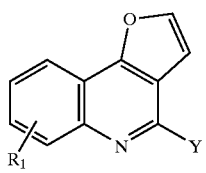 (A)

wherein $R_1$ is the same as that defined for formula (I'); and

Y represents: Cl, Br, or I;

with a compound of formula (B):

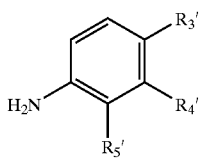 (B)

wherein $R_3'$, $R_4'$ and $R_5'$ are the same as those defined for formula (I').

20. The process as claimed in claim 19, wherein the compound of formula (B) is

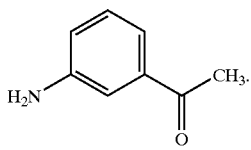

21. The process as claimed in claim 19, wherein the compound of formula (B) is

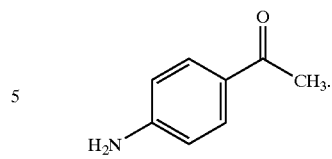

22. The process as claimed in claim 19, wherein the resultant compound of formula (I') is further treated with a compound of formula $NH_2OR$, in which R is H or a $C_1$–$C_4$ alkyl group, such that the

group in the

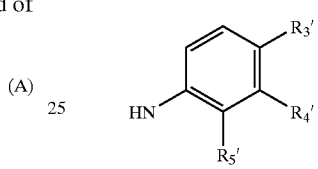

group of said compound of formula (I') is chemically modified to a

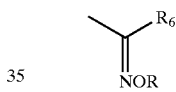

group, wherein R is H or a $C_1$–$C_4$ alkyl group.

23. The process as claimed in claim 19, wherein the resultant compound of formula (I') is further treated with a Lawesson's reagent or $P_2S_5$, such that the

group in the

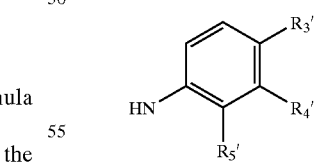

group of said compound of formula (I') is chemically modified to a

group.

24. The process as claimed in claim 19, wherein the resultant compound of formula (I') is further treated with benzyldimethylphosphinimide, such that the

group in the

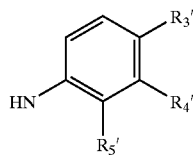

group of said compound of formula (I') is chemically modified to a

group.

25. The process as claimed in claim 19, wherein the resultant compound of formula (I') is further treated with $NH_2OH$ to chemically modify the

group in the

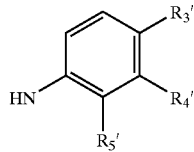

group of said compound of formula (I') to a

group, followed by a treatment with a $C_1$–$C_4$ alkyl halide to thereby modify the

group to a

group, wherein R is a $C_1$–C4 alkyl group.

26. The process as claimed in claim 19, wherein the compound of formula (A) is

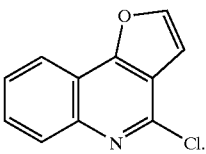

27. The process as claimed in claim 26, wherein the compound of formula (A) is formed from the reaction of

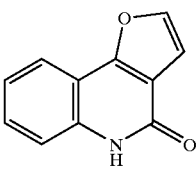

and $POCl_3$.

* * * * *